United States Patent [19]

Kiriyama

[11] Patent Number: 5,160,736
[45] Date of Patent: Nov. 3, 1992

[54] COMPOSITION FOR PREVENTION OR TREATMENT OF HYPERTRIGLYCERIDEMIA

[75] Inventor: Shuhachi Kiriyama, Hokkaido, Japan

[73] Assignee: Yamanouchi Pharmaceutical Co., Ltd., Tokyo, Japan

[21] Appl. No.: 641,494

[22] Filed: Jan. 15, 1991

[30] Foreign Application Priority Data

Jan. 17, 1990 [JP] Japan ................................ 2-8050

[51] Int. Cl.$^5$ ............................................ A61K 35/78
[52] U.S. Cl. .................................. 424/195.1; 514/886
[58] Field of Search ...................... 424/195.1; 514/866

[56] References Cited

FOREIGN PATENT DOCUMENTS 150515 9/1983 Japan .
800428 1/1987 Japan .

OTHER PUBLICATIONS

Komura, T. et al., Agric Biol Chem. 47(2): 383-87, 1983.

Primary Examiner—John W. Rollins
Attorney, Agent, or Firm—Burgess, Ryan & Wayne

[57] ABSTRACT

A composition for preventing or treating hypertriglyceridemia containing purple laver as an active ingredient is disclosed. A neutral fat level in blood can be reduced by ingesting the composition in a daily diet.

12 Claims, No Drawings

COMPOSITION FOR PREVENTION OR TREATMENT OF HYPERTRIGLYCERIDEMIA

FIELD OF THE INVENTION

This invention relates to a composition for prevention and treatment of hypertriglyceridemia. The composition of the invention finds its use as medicines, additives for foods, health foods, or physiological foods.

BACKGROUND OF THE INVENTION

Deaths of adults from arteriosclerotic diseases such as coronary diseases and cerebral vessel diseases have been increasing. It is hitherto known that hyperlipidemia is an important risk factor of these diseases. Hyperlipidemia is a condition in which one or both of cholesterol and neutral fats (mainly, triglycerides) among serum lipids increase. Primary hyperlipidemia which predominates hyperlipidemia is classified into 5 types of I to V according to the most received classification of WHO. Types I, IV, and V of primary hyperlipidemia are characterized by an increase in neutral fat level in the serum, and it is considered that neutral fats have greater influences than cholesterol (Beaumont, J.T. et al., *Classification of Hyperlipidemia and Hyperlipoproteinemia*, Bull WHO, Vol. 43, pp. 891–908 (1970)).

Type I and type V are inclusively called a chylomicronemia syndrome, and their relation to eruptive xanthoma, hepatosplenomegaly, pancreatitis, lipemia retinalis, etc. has been remarked. Further, type IV is a main factor of endogenous hypertriglyceridemia and, according to the report of the research and investigation team (team leader: Professor Tarui Seiichiro) on primary hyperlipidemia specified as a intractable disease by the Ministry of Health and Welfare, Japan (*Investigation Report in* 1986, p. 17, (1987)), it is present in 44.6% of male patients and 21.5% of female patients suffering from hyperlipidemia in Japan.

Endogenous hypertriglyceridemia has a relatively high incidence and is said to be often accompanied by obesity, diabetes or abnormal sugar tolerance, hyperinsulinemia, insulin resistance, hyperuricemia, etc.

Recently, reports supporting the theory that hypertriglyceridemia is an independent risk factor of diseases of coronary arteries have been increasing (M. Heikki Frick, et al., *N. Enql. J. Med.*, Vol. 317, p. 1237 (1989)).

Thus, neutral fats are now attracting attention as a risky factor in various diseases more than cholesterol.

It is believed that these hypertriglyceridemic conditions are induced to have their onset in association with single gene disorders or genetic predispositions combined with various environmental factors. Therefore, it is an effective method for preventing hypertriglyceridemia to habitually control an increase of neutral fats. More specifically, a neutral fat level can be controlled by avoiding overweighing, overeating or overdrinking, reducing the body weight, using moderation in drinking, controlling a sugar intake, regularly taking exercises, and the like. As a dietetic treatment, it is recommended to take polyenoic fatty acids while limiting a caloric intake.

Known treating agents for hypertriglyceridemia include Clofibrate drugs and nicotinic acid derivatives. In particular, Bezafibrate and Gemfibrozil are known to reduce especially neutral fats (Rogers R.L., et al., *Angiology*, Vol. 40, No. 4, Pt. 1, pp. 260–269 (1989), etc.).

In addition, various compositions effective to reduce neutral fats through a daily diet have been proposed. For example, a composition for treating hypertriglyceridemia which comprises an egg having a high iodine content as an active ingredient is disclosed in JP-B-1-48248 (corresponding to U.S. Pat. No. 4,394,376). (The term "JP-B" as used herein means an "examined published Japanese patent application".)

On the other hand, although purple laver is known as a highly nutritional food rich in protein, vitamins, and inorganic salts, it has been conventionally taken only as a favorite food or a taste-hitting food. There is no report on the effect of purple laver to reduce a blood neutral fat level.

Purple laver is also known to be effective in reducing cholesterol. For instance, JP-A-58-150515 (the term "JP-A" as used herein means an "unexamined published Japanese patent application") discloses a health food for reducing a cholesterol level in a living body, which is prepared by molding a purple laver powder mixed with a binder into granules, but no suggestion is made therein as to the action of reducing blood neutral fats. That is, as obviously implied by the above-described classification of hyperlipidemia, hypertriglyceridemai is distinguished from hypercholesterinemia. Drugs possessing an action of reducing cholesterol do not always possess an action of reducing neutral fats. For example, Probucol is a drug predominantly serving to reduce cholesterol, while Gemfibrozil is a drug predominantly serving to reduce neutral fats. From these facts, the composition for preventing or treating hypertriglyceridemia according to the present invention is distinguishable from the above-described health foods in range of application.

SUMMARY OF THE INVENTION

An object of the present invention is to provide a composition for preventing or treating hypertriglyceridemia, with which hypertriglyceridemia can be prevented or treated not by clinical pharmacotherapy but by oral ingestion through a daily diet.

The present invention relates to a composition for preventing or treating hypertriglyceridemia comprising purple laver as an active ingredient.

The inventors have investigated nutritional functions of purple laver, particularly actions on lipid metabolism. As a result, it has unexpectedly found that purple laver has an effect in reducing neutral fats in blood plasma of rats. It has been further ascertained that purple laver has not only an effect on abnormal hypertriglyceridemia of experimental animals caused by feeding on a highly calorific diet but also an effect of reducing neutral fats in the plasma of rats fed on a general diet. The present invention has been completed based on these findings.

DETAILED DESCRIPTION OF THE INVENTION

The composition according to the present invention accomplishes preventive and treating effects on hypertriglyceridemia through a daily diet.

The terminology "purple laver" as used herein is a seaweed belonging to the *Rhodophycophyta* division, the *Porphyra* genus (e.g., *Porphyra tenera* KJELLMAN, *Porphyra yezoensis* VEDA), which has hitherto been eaten as food, especially in Japan, and includes unroasted sheeted purple laver, dried sheeted purple laver, and any other processed products of purple laver. A preferred composition of the present invention comprises a purple laver powder obtained by powderizing dried purple laver. An example for preparing a purple laver powder is described below.

Preparation of Purple Layer Powder

Raw purple laver collected from sea water (grown in Ehime, Japan) is washed with water for several minutes, dehydrated at a high speed for several minutes, and artificially dried at 38° C. to 40° C. for about 2 hours to obtain dried raw purple laver having a water content of from 12 to 13% by weight. The resulting dried raw purple laver was piled to a height of about 5 cm and dried in hot air at about 60° C. for about 10 to 15 minutes. For the purpose of preventing moisture absorption, the dried laver was treated successively in a power mill in which the laver is passed through an about 5 cm mesh screen and in a sample mill in which the laver is passed through about a 1 mm mesh screen to obtain a laver powder. The resulting laver powder is packed and preserved in a polyethylene container sealed with a cap equipped with a desiccant.

A purple laver powder may also be prepared by treating a commercially available sun-dried raw purple laver (ready to be powdered on crumpling) or a freeze-dried product of raw purple laver by means of the above-described power mill and sample mill.

The thus obtained purple laver powder can be used as such as the composition for preventing and treating hypertriglyceridemia according to the present invention. If desired, the laver powder in combination with a binder may be subjected to powderization or granulation, or the laver powder in combination with various adjuvants, such as vehicles and binders, may be formulated into tablets, capsules or the like form.

Adjuvants which can be used in the present invention include binders, e.g., starch, gum arabic, gelatin, sorbitol, tragacanth gum, and polyvinylpyrrolidone; vehicles, e.g., lactose, sugar, corn starch, calcium phosphate, and glycine; and lubricants, e.g., magnesium stearate, talc, polyethylene glycol, and silica.

According to the data furnished by National Federation of Fisheries Co-operative Association, Japan, the consumption of purple laver in Japan in 1987 amounts to about 9,600,000,000 sheets (about 30,000 tons), which corresponds to a daily intake of about 0.6 g for each Japanese. Such a low intake of purple laver, usually taken in the form of a roasted purple laver sheet or a seasoned and dried purple laver sheet, cannot be expected to exhibit a preventive and treating effect on hypertriglyceridemia. In general, purple laver exerts its effect as expected when continuously ingested in an amount of from about 1 to 50 g, and preferably from about 5 to 40 g, (as a laver powder) per day for an adult. Having been conventionally used as food, purple laver has no toxicity even when ingested in such a large quantity.

Such a purple laver intake reduces a neutral fat level in hypertriglyceridemia. In particular, for persons having predispositions to hypertriglyceridemia, the ingestion of purple laver reduces the neutral fat level in blood through a daily diet to prevent the onset of hypertriglyceridemia. As a matter of course, it prevents a blood neutral fat level in normal persons from increasing due to overweighing, overeating, overdrinking, and the like.

The purple laver in the form of powders, dusts, granules, tablets, capsules, etc. can also be used as an additive for various foods, and the foods containing these preparations serve as health foods for their high protein content or physiological foods for their effects to prevent or treat hypertriglyceridemia.

Where the purple laver preparation is added to various foods, the amount to be added is appropriately selected depending on the food processing method and the characteristics, taste or appearance of the food. From the viewpoint of preventive or curative effects on hypertriglyceridemia, it is desirable to add purple laver in a proportion as large as possible.

Thus, the purple laver preparation to be used as a food additive preferably has a form ready to be added to various foods in a large quantity. Foods to which the purple laver preparation may be added preferably include those which permit of incorporation of a large quantity of purple laver and those which are usually ingested in quantity. Examples of such foods include staple foods, e.g., breads, noodles, and pastes; cookies, pastries, TOFU (bean curd), pasted sea foods, MISO (a Japanese seasoning prepared from soybeans), etc. These foods, when continuously ingested in a daily diet, produce preventive or curative effects on hypertriglyceridemia.

The effects of the composition for preventing or treating hypertriglyceridemia according to the present invention are demonstrated by the following test examples. All the percents are by weight unless otherwise indicated.

TEST EXAMPLE 1

Test Animals

SD male rats (initial body weight: about 140 g) were maintained on a diet containing 20% casein as shown in Table 1 below (hereinafter referred to as 20% casein diet) for 10 days. A plasma cholesterol level of each animal was measured. After that, the rats were divided into 6 groups each consisting of 6 animals in such a manner that each group might have the equal average body weight and the equal average plasma cholesterol level, and used for the following experimentation.

Test Method

Each test group was fed on each of the diets shown in Table 1 for 8 days. The protein sources used in diets and their nitrogen content were as follows.

Casein ... 134 mg-nitrogen/g
Egg yolk ... 122 mg-nitrogen/g
Sardine ... 148 mg-nitrogen/g
Isolated soybean protein ... 137 mg-nitrogen/g
Purple laver (laver powder prepared as described above) ... 62.9 mg-nitrogen/g
Wheat gluten ... 125 mg-nitrogen/g The amount of the protein source to be added to each diet was adjusted so as have the same nitrogen content as the 20% casein diet. Since purple laver has a high dietary fiber content, the diet containing the same as a protein source contained 18% of dietary fiber. In order to correct this, 18% of cellulose was added to other diets.

On the final day of the experimentation (8th day), the body weight was measured, and blood was taken from the aorta abdominalis under anesthesia, and the neutral fat level was measured by using TG-EN KAINOS (a trade name of Kainos Co., Ltd.).

The measured values were statistically analyzed by one-way analysis of variance (ANOVA), and a significant difference of the average among groups was determined by Duncan's multiple range test. The results obtained are shown in Tables 2 and 3 below.

TABLE 1

| Composition (%): | Composition of Diet | | | | | |
|---|---|---|---|---|---|---|
| | Casein | Egg Yolk | Sardine | Isolated Soybean Protein | Purple Laver | Wheat Gluten |
| Protein source | 20 | 22 | 18.1 | 19.6 | 42.6 | 21.4 |
| Corn oil | 5 | 5 | 5 | 5 | 5 | 5 |
| Mineral mixture | 4 | 4 | 4 | 4 | 4 | 4 |
| Vitamine mixture | 1 | 1 | 1 | 1 | 1 | 1 |
| Choline chloride | 0.2 | 0.2 | 0.2 | 0.2 | 0.2 | 0.2 |
| Vitamin E granules | 0.1 | 0.1 | 0.1 | 0.1 | 0.1 | 0.1 |
| Sucrose | 51.7 | 49.7 | 53.6 | 52.1 | 47.1 | 50.3 |
| Cellulose | 18 | 18 | 18 | 18 | — | 18 |
| Total | 100 | 100 | 100 | 100 | 100 | 100 |

TABLE 2

| | Final Body Weight and Food Intake | |
|---|---|---|
| Test Group | Final Body Weight* (g) | Food Intake (g/8 days) |
| Casein | 270.2 ± 6.3a** | 177.1 ± 6.3b** |
| Egg yolk | 270.7 ± 5.0a | 191.0 ± 6.6ab** |
| Sardine | 273.8 ± 4.5a | 178.5 ± 5.5b |
| Isolated bean protein | 271.8 ± 3.7a | 200.8 ± 5.5a |
| Purple laver | 268.3 ± 5.7a | 149.7 ± 5.5b |
| Wheat gluten | 238.5 ± 5.5b | 170.6 ± 9.7b |

Note:
*The average initial body weight was 216.8 ± 1.4 g.
**The results of Duncan's multiple range test were expressed by small alphabets. Groups marked with the same alphabet had no significant difference. For example, there was no significant difference between experimental groups marked with a (hereinafter the same).

TABLE 3

| Neutral Fat Level in Plasma | |
|---|---|
| Test Group | Triglyceride Concn. in Plasma (mg/dl) |
| Casein | 231.7 ± 23.8a |
| Egg yolk | 271.1 ± 28.7a |
| Sardine | 233.5 ± 31.4a |
| Isolated soybean protein | 134.1 ± 8.2b |
| Purple laver | 152.3 ± 17.2b |
| Wheat gluten | 202.3 ± 18.8ab |

Evaluation

As shown in Table 2, the rate of growth was not influenced by the kind of protein sources, except for wheat gluten. That is, no significant changes in body weight was observed among the groups on the final day, except for wheat gluten. The fact that the food intake of the purple laver group was significantly lower than that of any other group appears to indicate that the low intake gave no influences on growth rate because of high nutritive qualities of purple laver.

The groups fed on the isolated soybean protein diet and the purple laver diet showed a significant lower level of neutral fats in the plasma than the group fed on the casein diet, sardine diet or egg yolk diet, as shown in Table 3.

From these experimental results, it is apparent that purple laver has an effect in reducing neutral fats in the plasma without affecting the growth rate. It was also proved that such an effect of purple laver is equal to or even greater than that produced by isolated soybean protein which has recently attracted attention as a protein source having a lipid reducing effect.

TEST EXAMPLE 2

Test Animals

SD male rats (initial body weight: about 140 g) were maintained on a basic diet containing 25% casein shown in Table 4 below (hereinafter referred to as 25% casein basic diet) for 12 days. After that, the rats were divided into 5 groups each consisting of 6 animals in such a manner that each group had the same average body weight, and used for the following experimentation.

TABLE 4

| Composition of 25% Casein Basic Diet | |
|---|---|
| Component | Content (%) |
| Casein | 25 |
| Corn oil | 5 |
| Mineral mixture | 4 |
| Vitamine mixture | 1 |
| Choline chloride | 0.2 |
| Vitamin E granules | 0.1 |
| Sucrose | 64.7 |
| Total | 100 |

Test Method

Each group was fed on the 25% casein basic diet or the 25% casein basic diet to which were added 20.9% of the laver powder prepared as described above, 10% of agar, 10% of green asparagus or 10% of cellulose as a dietary fiber source for 28 days.

On the final day of experimentation (28th day), the body weight was measured. Further, blood was collected from the aorta abdominalis under anesthesia, and the neutral fat concentration in the plasma was measured.

The results of experiments were statistically analyzed by one-way analysis of variance (ANOVA), and a significant difference of the average among groups was determined by Duncan's multiple range test. The final body weight and the food intake for 8 days are shown in Table 5 below, and the neutral fat concentrations are shown in Table 6 below.

TABLE 5

| | Final Body Weight and Food Intake | |
|---|---|---|
| Test Group | Final Body Weight* (g) | Food Intake (g/8 days) |
| Casein | 386.0 ± 12.8a | 618.2 ± 24.1ab |
| Casein + Purple laver | 397.3 ± 4.0a | 614.2 ± 7.9b |
| Casein + Agar | 401.3 ± 9.7a | 678.2 ± 21.8a |
| Casein + Asparagus | 398.2 ± 11.1a | 629.2 ± 22.9ab |

TABLE 5-continued

Final Body Weight and Food Intake

| Test Group | Final Body Weight* (g) | Food Intake (g/8 days) |
| --- | --- | --- |
| Casein + Cellulose | 402.5 ± 7.9a | 656.1 ± 17.3ab |

Note:
*The initial average body weight was 235.4 ± 1.6 g.

TABLE 6

Neutral Fat Concentration in Plasma

| Test Group | Triglyceride (mg/dl) |
| --- | --- |
| Casein | 427.1 ± 37.4a |
| Casein + Purple laver | 243.0 ± 38.5b |
| Casein + Agar | 386.4 ± 92.9ab |
| Casein + Asparagus | 374.3 ± 56.8ab |
| Casein + Cellulose | 346.1 ± 37.5ab |

Evaluation

In the above experiment, whether an increase in neutral fat level in the plasma induced by casein could be reduced by addition of various dietary fibers was examined over about 1 month. No significant difference in final body weight was observed among groups, indicating that the growth of the animals showed no difference depending on the kind of dietary fiber added as shown in Table 5.

However, the neutral fat concentration was significantly reduced in the purple laver group as shown in Table 6. From these results, it is apparent that purple laver is superior to other various dietary fibers in the effect of reducing neutral fats.

Thus, purple laver was proved to have excellent effects to reduce neutral fats as compared with either various other proteins or various other dietary fibers.

As described above, the composition for preventing or treating hypertriglyceridemia containing purple laver as an active ingredient can be orally taken through a daily diet thereby to reduce neutral fats in blood and to prevent or treat diseases associated with hypertriglyceridemia.

The composition of the present invention can be used as an additive for various foods. Foods added with the composition have ensured nutritional values and increased effects to prevent or treat the above-described diseases and are therefore useful as health foods or physiological foods.

The present invention is now illustrated in greater detail with reference to Examples, but it should be understood that the present invention is not deemed to be limited thereto. All the percents and parts are by weight unless otherwise specified.

EXAMPLE 1

To the purple laver powder as above prepared was added an equivalent amount of a 5% aqueous solution of corn starch, and the mixture was kneaded in a kneader and granulated to obtain granules having a diameter of about 300 μm. The granules were dried in warm air to obtain raw laver granules.

For prevention or treatment of hypertriglyceridemia, a preferred intake of the resulting raw laver granules is from about 5 to 30 g per day for an adult.

EXAMPLE 2

Twenty parts of the purple laver powder as above prepared and 80 parts of wheat flour were mixed, and to the mixed powder were added 3 parts of sugar, 2 parts of edible salt, and 3 parts of a shortening. The mixture was kneaded while adding 50 parts of water. A solution of 2 parts of yeast in 6 parts of water was then added thereto, followed by thoroughly kneading. The resulting dough was fermented at about 28° C for 2 hours. After degassing, the fermentation was further continued, and the dough was divided into several equal masses. After proofing, the dough was shaped, put in a mold, and baked at 200° C. to 280° C. to obtain bread containing a large amount of purple laver.

EXAMPLE 3

A mixture of 160 parts of wheat flour, 4 parts of edible salt, and 10 parts of the purple laver powder as above prepared was kneaded with 32 parts of water. The resulting dough was rolled out by means of a rolling machine, cut to noodles by means of a noodle cutter, and dried to obtain noodles containing a large amount of purple laver.

EXAMPLE 4

A mixture of 100 parts of wheat flour, 5 parts of sugar, 10 parts of a shortening, 20 parts of the laver powder as above prepared, 0.4 part of saleratus (sodium bicarbonate), 0.6 part of ammonium carbonate, and 0.5 part of edible salt was kneaded with 18 parts of water. The dough was shaped and baked at 150° to 250° C. to obtain crackers containing a large amount of purple laver.

EXAMPLE 5

A hundred parts of soybean milk, 20 parts of laver powder prepared from dried raw purple laver, and 0.1 part of gelatin were mixed, and 0.5 part of bittern was added thereto. The precipitate thus formed was then allowed to solidify in a mold to obtain TOFU (soybean curd) containing a large amount of purple laver.

EXAMPLE 6

Sixty parts of minced tuna, 40 parts of minced whale meat, and 3 parts of edible salt were mixed up, and to the mixture were added 30 parts of the laver powder as above prepared, 1 part of sugar, and small amounts of glutamic acid, starch, flavors, antiseptics, pyroligneous acid, vitamin A, etc. A shortening oil was further added thereto. The mixture was packed and sealed in a casing and sterilized by soaking in hot water at 85° to 88° C. for 50 minutes, followed by cooling to obtain fish sausage containing a large amount of purple laver.

EXAMPLE 7

Twelve parts of rice were allowed to absorb water in a usual manner and smothered. After allowing to cool, the smothered rice was inoculated with koji mould to produce koji. The resulting koji was mixed with 30 parts of smothered soybean, 20 parts of the laver powder as above prepared, and water were mixed up and chopped. The mixture was fermented in a fermenter at 26° to 28° C. for about 75 days and finally strained to obtain MISO containing a large amount of purple laver.

EXAMPLE 8

Ten parts of the laver powder as above prepared were added to a mixture of 100 parts of durum flour, a small amount of an egg, and 3 to 4 parts of edible salt. Water was added thereto, and the mixture was stirred and kneaded. The resulting dough was appropriately rolled out to obtain paste having a water content of about 30%. The paste as such or stuffed with meats, cheese, vegetables, etc. was heated at about 100° C. for 2 minutes and packaged to obtain a preservable paste product.

While the invention has been described in detail and with reference to specific examples thereof, it will be apparent to one skilled in the art that various changes and modifications can be made therein without departing from the spirit and scope thereof.

What is claimed is:

1. A method for preventing hypertriglyceridemia in a warm-blooded animal susceptible to hypertriglyceridemia, comprising orally administering an effective amount of purple laver to a warm blooded animal.

2. The method of claim 1, wherein said purple layer is in the form of a powder prepared by drying raw purple laver in hot air at about 60° C.

3. The method of claim 1 comprising orally administering from 1 to 50 grams per day of said purple laver to said warm-blooded animal.

4. The method of claim 3 comprising orally administering from 5 to 40 grams per day of said purple laver to said warm-blooded animal.

5. The method of claim 1 wherein said purple laver is administered in combination with an ingestible carrier.

6. The method of claim 5, wherein said ingestible carrier is selected from the group consisting of binders, adjuvants and solid and liquid foods.

7. A method for treating hypertriglyceridemia in a warm-blooded animal in need of such treatment, comprising orally administering an effective amount of purple laver to a warm-blooded animal.

8. The method of claim 7, wherein said purple laver is in the form of a powder prepared by drying raw purple laver in hot air at about 60°.

9. The method of claim 7, wherein said purple laver is administered in combination with an ingestible carrier.

10. The method of claim 9, wherein said ingestible carrier is selected from the group consisting of binders, adjuvants and solid and liquid foods.

11. The method of claim 7 comprising orally administering from 1 to 50 grams per day of said purple laver to said warm-blooded animal.

12. The method of claim 11 comprising orally administering from 5 to 40 grams per day of said purple laver to said warm blooded animal.

* * * * *